United States Patent [19]
Duffin, Jr. et al.

[11] Patent Number: 5,374,279
[45] Date of Patent: Dec. 20, 1994

[54] SWITCHABLE CONNECTOR BLOCK FOR IMPLANTABLE DEFIBRILLATOR

[75] Inventors: Edwin G. Duffin, Jr.; Warren S. Watson, both of New Brighton, Minn.; Karel F. A. A. Smits, Oirsheek, Netherlands

[73] Assignee: Medtronic, Inc., Minneapolis, Minn.

[21] Appl. No.: 968,737

[22] Filed: Oct. 30, 1992

[51] Int. Cl.⁵ ............................................ A61N 1/39
[52] U.S. Cl. ........................................ 607/5; 607/37
[58] Field of Search ............... 607/36, 38, 37, 123, 607/5

[56] References Cited

U.S. PATENT DOCUMENTS

| | | | |
|---|---|---|---|
| 4,301,805 | 11/1981 | Peers-Trevarton et al. | 128/419 P |
| 4,445,511 | 5/1984 | Cowdery et al. | 607/37 |
| 4,595,009 | 6/1986 | Leinders | 128/419 D |
| 4,641,656 | 2/1987 | Smits | 128/419 D |
| 4,693,253 | 9/1987 | Adams | 128/419 D |
| 4,727,877 | 3/1988 | Kallok | 128/419 D |
| 4,817,634 | 4/1989 | Holleman et al. | 128/784 |
| 4,830,006 | 5/1989 | Haluska et al. | 128/419 PG |
| 4,953,551 | 9/1990 | Mehra et al. | 128/419 D |
| 4,958,632 | 9/1990 | Duggan | 128/419 PG |
| 5,014,696 | 5/1991 | Mehra | 128/419 D |
| 5,044,374 | 9/1991 | Lindemans et al. | 128/784 |
| 5,095,902 | 3/1992 | Ljungstroem | 607/37 |
| 5,129,394 | 7/1992 | Mehra | 128/419 PG |
| 5,235,977 | 8/1993 | Hirschberg et al. | 607/123 |

FOREIGN PATENT DOCUMENTS

9117792  11/1991  WIPO .................. 607/36

*Primary Examiner*—Angela D. Sykes
*Assistant Examiner*—Kennedy J. Schaetzle
*Attorney, Agent, or Firm*—Reed A. Duthler; Harold R. Patton

[57] ABSTRACT

A medical electrical pulse generator having a switchable connector assembly. The connector assembly is provided with connector bores, each intended to receive a medical electrical lead or a sealing plug, if no lead is provided. Electrical connectors located within the bores are arranged such that interconnection of the pulse generator circuitry within the device and electrodes on the leads and/or housing of the device can be altered by means of connector pins located on the electrical leads or the sealing plugs, which may be employed to interconnect electrical connectors within a connector bore.

15 Claims, 10 Drawing Sheets

SWITCHABLE CONNECTOR BLOCK FOR IMPLANTABLE DEFIBRILLATOR

BACKGROUND OF THE INVENTION

This invention relates generally to electrical stimulators and more particularly to implantable cardioverters and defibrillators.

Implantable stimulator, including pacemakers, cardioverters and defibrillators have been proposed which employ multi-electrode systems for sensing cardiac signals and delivery of pacing, cardioversion or defibrillation pulses. Switching between various electrode configurations in order to optimize the therapy being delivered has often been suggested. For example, U.S. Pat. No. 4,958,632, issued to Duggan et al. discloses an early microprocessor controlled pacemaker provided with switching circuitry which allows the device to be operated in unipolar or bipolar mode. Similarly, in the context of implantable cardioverters and defibrillators, internal switching circuitry for allowing selection of particular electrode configurations out of three or more available electrodes have been widely disclosed. For example, U.S. Pat. No. 5,129,394, issued to Mehra discloses such a system.

It has also been proposed to employ a switch located in a connector block to switch between unipolar and bipolar electrode configurations in the context of cardiac pacing, as disclosed in U.S. Pat. No. 4,301,805 issued to Peers Trevarton et al or to employ a switch located in or on the lead body to switch between multiple electrodes in the context of a defibrillation lead, as disclosed in allowed U.S. patent application Ser. No. 07/621,112, filed Nov. 30, 1990 by Pohndorf et al.

In use of clinically available implantable defibrillators which provide for use of three or more defibrillation electrodes, it is not always the practice to implant such devices with all available leads present. In some cases, the physician may desire to implant only two of three available leads, leaving one connector bore within the connector assembly of the device unfilled. In the context of the Medtronic Model 7216 and 7217 implantable pacemaker/cardioverter/defibrillators, a plug is provided to fill the unused connector bore, to prevent fluid ingress.

SUMMARY OF THE INVENTION

The present invention comprises a switchable connector assembly which provides for a simple mechanism for switching between electrode systems employing different numbers of leads, while simultaneously providing a mechanism to seal unused connector bores, when less than all available leads are employed. The invention accomplishes these objects by provision of a sealing plug which is inserted into the unused connector bore, and which also includes a conductive element which establishes a connection internal to the connector assembly which interconnects the defibrillator or cardioverter output stage and one or more of the electrical connectors located within the connector assembly. No reprogramming of the device is required in order to accomplish the electrode configuration change.

In a first embodiment of the invention, a first connector block is provided coupled to the external conductive housing of the device, located on the same connector bore as a second connector block coupled to one of the output terminals of the cardioverter/defibrillator circuitry within the device. In this embodiment, insertion of a defibrillation lead connector assembly into the connector bore normally connects the electrode on the lead to the second connector block and thus to the defibrillator circuitry, leaving the device housing unconnected. In the event that the device housing is desired to be used as an electrode, a sealing plug carrying an elongated conductive pin is inserted, electrically connecting the first and second connector blocks to one another, thus coupling the housing to the defibrillator output circuitry, and simultaneously sealing the unused connector bore.

This first embodiment has as an additional object, an enhancement of the safety of the operation of the device, in that the housing of the device remains unconnected until the sealing plug is inserted, allowing for safe handling of the device by a physician without fear of electrical shock should the device be inadvertently be activated. The first embodiment of the invention also has the advantage that it may be practiced using a defibrillation electrode lead carrying an elongated connector pin. This elongated pin, similar to the pin on the sealing plug, is inserted into the connector lumen, simultaneously coupling the defibrillator output circuitry to both a defibrillation electrode located on the lead and to the housing of the device to provide a multi-electrode, simultaneous pulse system, without the necessity of reprogramming the device.

A second embodiment of the device also provides the ability to switch between electrode systems employing differing numbers of leads. For example, a lead carrying defibrillation electrodes located in the right ventricle and coronary sinus may be provided, with the defibrillation electrode located in the right ventricle coupled to a first connector block within a first connector bore within the connector assembly, which connector block is not directly connected to the output circuitry of the defibrillator. In a second bore, a second connector block is provided which is directly coupled to an output of the defibrillator circuitry, along with a third connector block which is coupled only to the first connector block. In the event that it is desired to deliver defibrillation pulses between the superior vena cava and right ventricular electrodes, a sealing plug carrying an elongated conductive pin, as discussed above in conjunction with the first embodiment may be inserted, bridging the second and third connector blocks within the second connector bore and thereby connecting the output of the defibrillator circuitry to the right ventricular electrode. Alternatively, a separate defibrillation electrode lead, for example a left ventricular patch electrode lead may be inserted, into the second connector bore and its electrode coupled directly to the output of the defibrillator circuitry by means of the first connector block, allowing for delivery of the defibrillation pulses between the superior vena cava and patch electrodes. This second embodiment, like the first embodiment provides for a change between the two available electrode configurations without the necessity of programming, and simultaneously provides a seal for a connector bore which would normally be used in conjunction with one of the electrode systems.

DETAILED DESCRIPTION OF THE PREFERRED EMBODIMENTS

Figure 1:
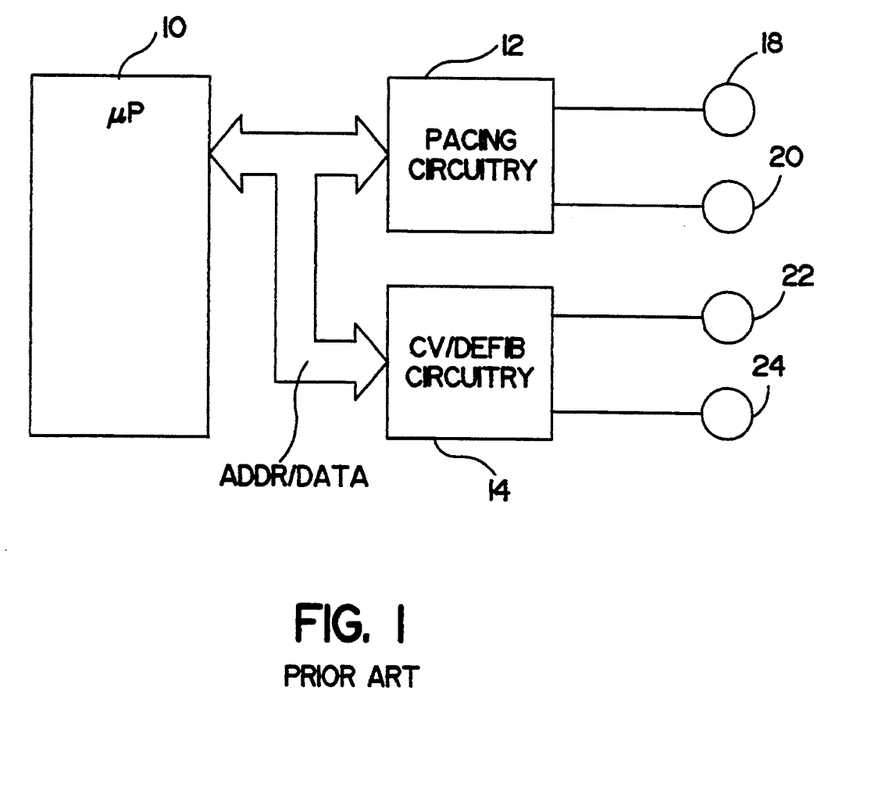
FIG. 1 is a block diagram of a prior art implantable pacemaker/cardioverter/defibrillator.

FIG. 1 is a block diagram of a prior art implantable pacemaker/cardioverter/defibrillator. For example, the device may be an implantable/cardioverter/defibrillator as described in U.S. Pat. No. 5,129,414 issued to Mehra, U.S Pat. No. 4,595,009 issued to Leinders et al or U.S. Pat. No. 4,693,253 issued to Adams, or U.S. Pat. No. 4,830,006, issued to Haluska et al, all of which are incorporated by reference in their entireties. For purposes of understanding the present invention, it is only necessary to note that the device is controlled by a microprocessor 10, including a random access memory which carries which carries a program which defines its operational modes, and that the stored program in the microprocessor controls operation of pacing circuitry 12 and cardioversion/defibrillation circuitry 14 via address/data bus 16. The pacing circuitry is provided with input/output terminals 18 and 20, which are employed to deliver pacing pulses to pace the heart and are employed to sense cardiac depolarizations, as generally practiced in conjunction with demand pacing and/or anti-tachyarrhythmia pacing. The cardioversion/defibrillation circuitry is provided with two output terminals, 20 and 24, which provide high voltage cardioversion and defibrillation pulses. The present invention provides a mechanism for selecting the interconnection between cardioverter/defibrillator output terminals 22 and 24 and a variety of leads and electrodes. The present invention is believed usable in conjunction with any prior art cardioverter/defibrillator.

Figure 2:
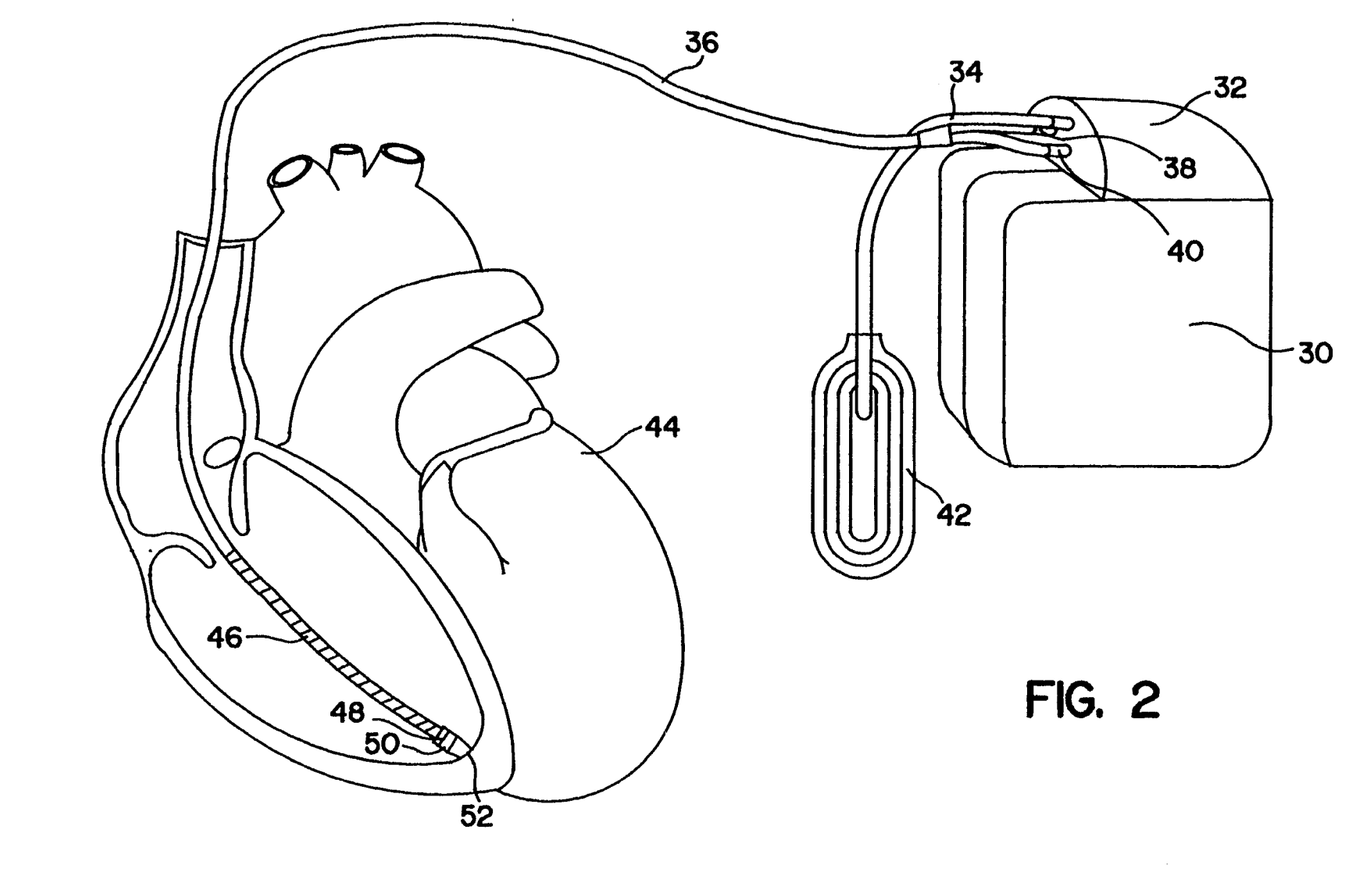
FIG. 2 is an illustration of a pacemaker/cardioverter/defibrillator and an associated lead system in conjunction with a human heart.

FIG. 2 is an illustration of a pacemaker/cardioverter/defibrillator and an associated lead system in conjunction with a human heart 44. The device housing 30 is fabricated of a conductive metal such as titanium or stainless steel, and as discussed below, may function as an electrode surface. The connector housing 32 is typically fabricated of epoxy or other plastic material, and is provided with three connector bores.

Inserted into two connector bores are two legs 38 and 40 of a bifurcated connector assembly located on right ventricular defibrillation lead 36. Lead 36 may correspond to the right ventricular defibrillation electrode lead disclosed in the above cited patent issued to Mehra. The lead includes an elongated coil electrode 46 located in the right ventricle of heart 44, a ring electrode 48 located on an insulative head assembly 50 which contains an advanceable helical electrode 52. Cardiac pacing and sensing is accomplished using electrodes 50 and 52, while electrode 46 is used for defibrillation and cardioversion.

Figure 4:
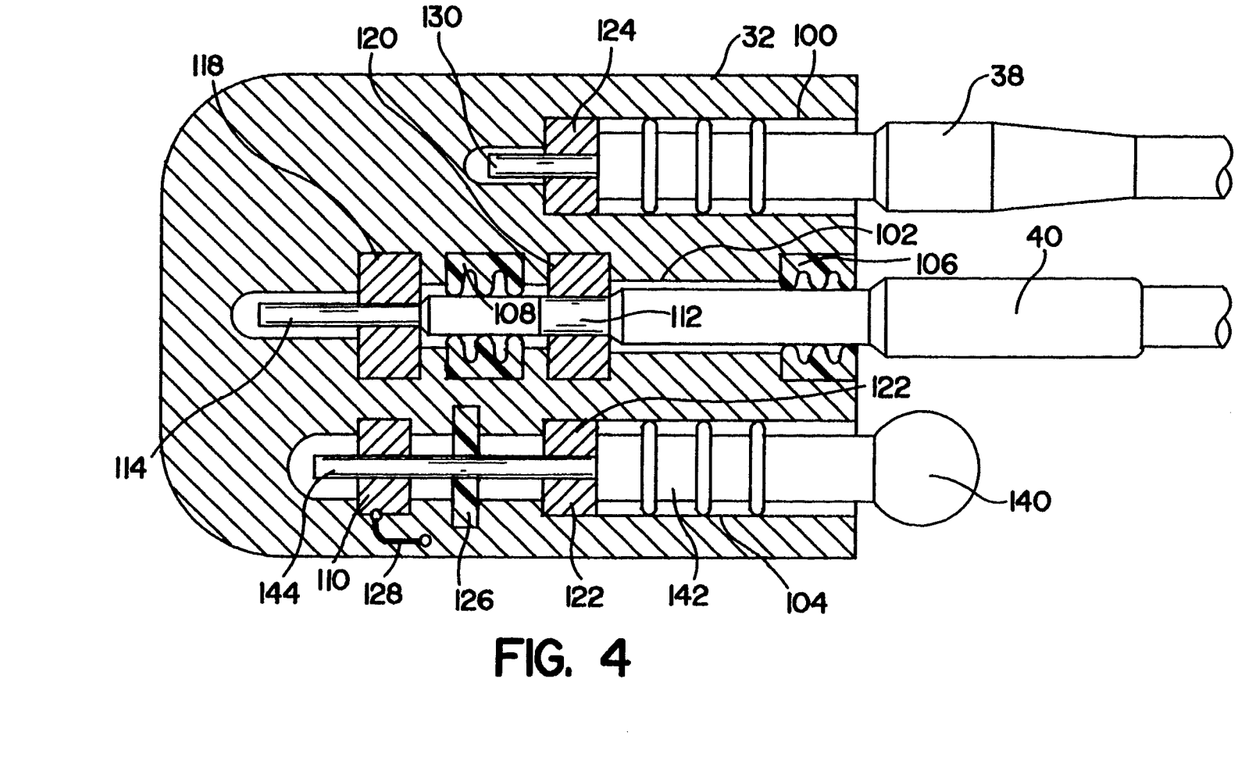
FIG. 4 is a cutaway view of the connector housing illustrated in FIG. 3, with a lead removed and a sealing plug inserted.
Figure 5:
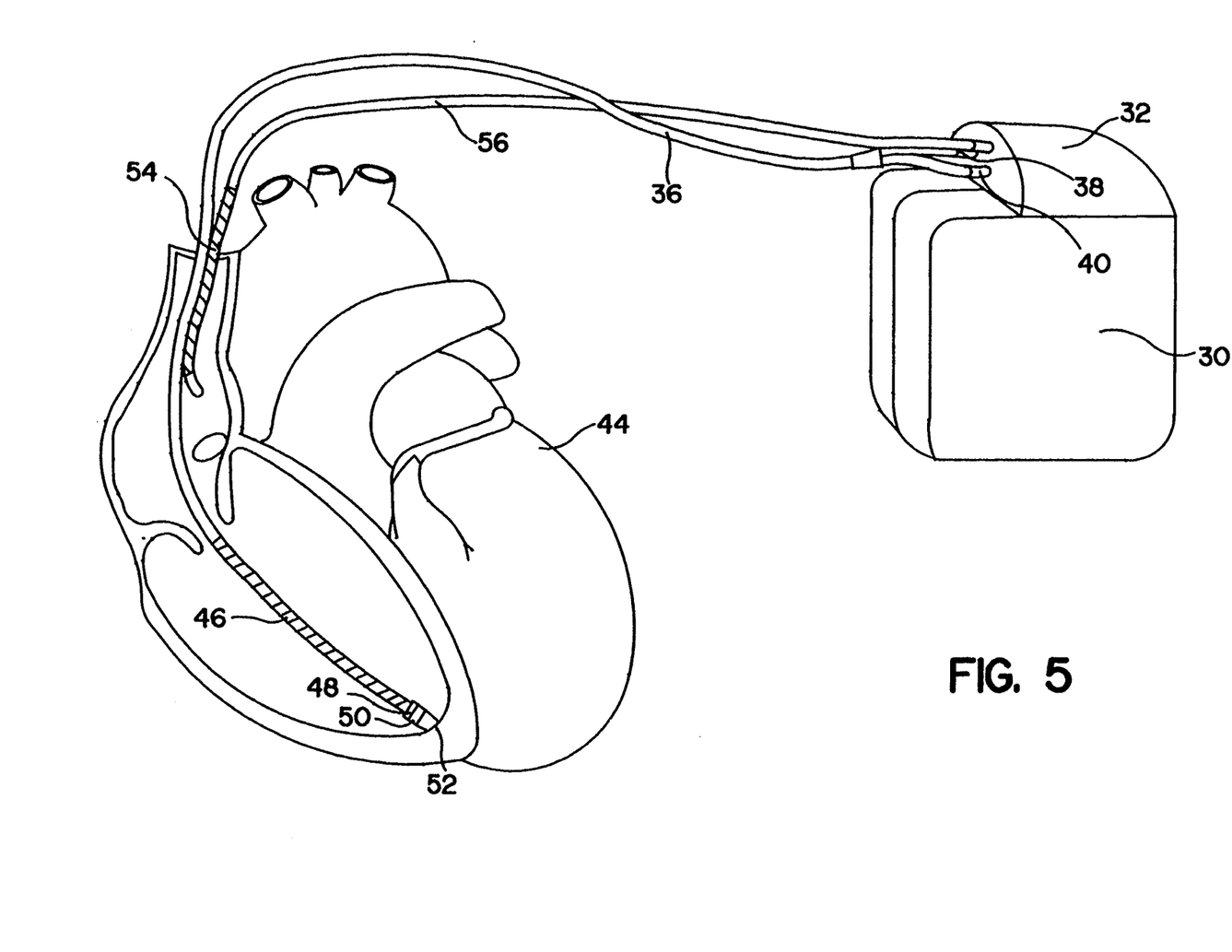
FIG. 5 illustrates the implantable pacemaker/cardioverter/defibrillator of FIG. 2 with an alternate lead system.

A second, subcutaneous electrode lead 34 is illustrated which carries a subcutaneous electrode 42, which may correspond to the electrode illustrated in U.S. Pat. No. 5,044,374, issued to Lindemans et al and incorporated herein by reference in its entirety. As discussed below, the present invention, as illustrated in FIGS. 3-5 allows for switching between the use of subcutaneous electrode 42 and housing 30 of the pacemaker, without reprogramming, and also provides a mechanism to seal the connector bore, which otherwise would have served to connect lead 34 to the output circuitry of the cardioverter/defibrillator.

Figure 3:
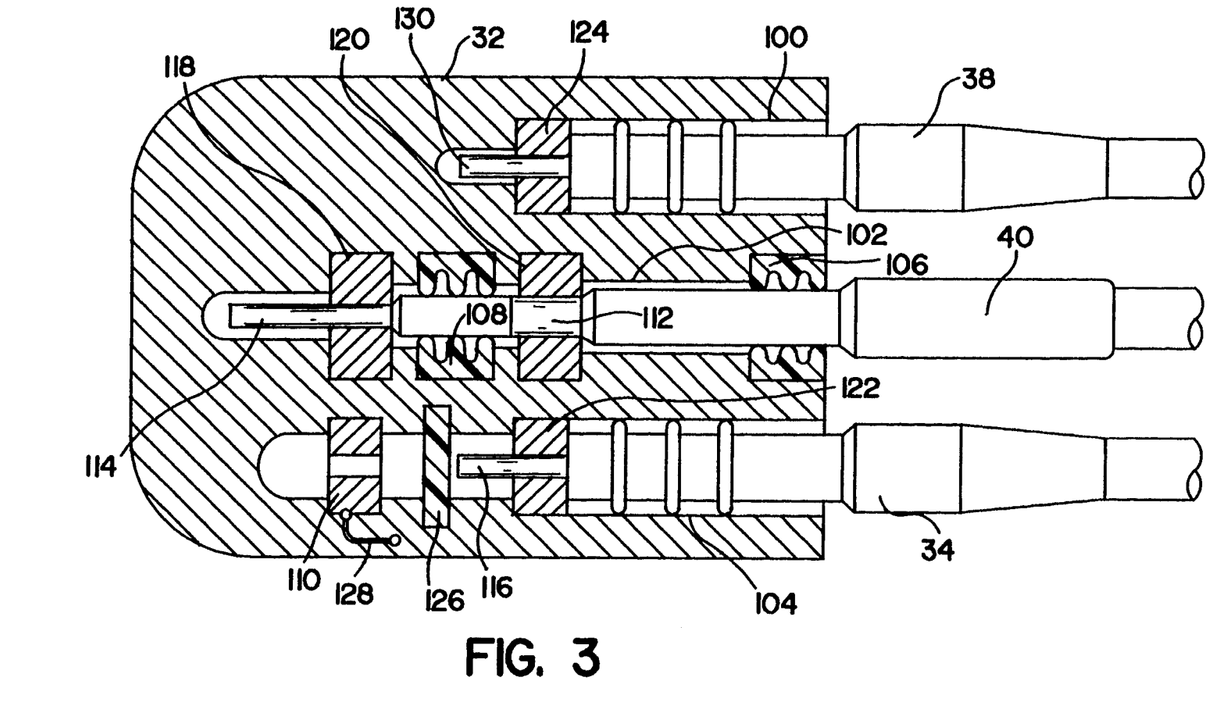
FIG. 3 is a cutaway view illustrating the internal structure of the connector housing of the device of FIG. 2 in conjunction with connectors of the associated lead system.

FIG. 3 is a cutaway view illustrating the internal structure of connector housing 32. In this view, all three connector bores are shown as located parallel to one another in essentially same plane. This configuration is not excepted to be employed in most cases, but has been chosen for FIGS. 3, 4 and 6 for purposes of clarity of illustration. As a practical matter, it is to be expected that the connector bores will be stacked in some fashion, for example as illustrated in FIG. 2.

Three connector bores 100, 102 and 104 are provided within connector housing 32. Connector bore 100 is provided with an electrical connector block 124 which is coupled to one output of the cardioverter/defibrillator circuitry. As illustrated, one leg 38 of lead 36 is inserted into bore 100. Connector leg 38 carries a conductive pin 130 which couples connector block 124 to elongated electrode 46 on lead 36 (FIG. 1). Connector block 124 may make contact with pin 130 by means of a set screw, a spring member, or other conventional mechanism for making electrical contact, as is the case in conjunction with all other connector blocks discussed herein.

The other leg 40 of lead 36 is inserted into connector bore 102, which is provided with a set of circumferential sealing rings 106, sealing the point of entry. Connector bore 102 is provided with two connector blocks 118 and 120, which are coupled to terminals 18 and 20 in FIG. 1, and serve to couple the pacing circuitry 12 (FIG. 1) to electrodes 48 and 52 (FIG. 2) via connector pin 114 and connector ring 112. Sealing rings 108 prevent fluid leakage between connector blocks 118 and 120.

The proximal end of lead 34 is similarly inserted into connector bore 104, which is provided with two connector blocks 110 and 122. Connector 122 corresponds to connector block 22 (FIG. 1), and is coupled to the cardioverter/defibrillator output circuitry. With lead 34 inserted as illustrated, defibrillation and cardioversion pulses are delivered between electrodes 46 and 42 (FIG. 2). Connector bore 104 is also provided with a second connector block 110, which is coupled by means of a jumper wire 128 to the upper surface of the conductive housing 30 of the implantable pacemaker/cardioverter/defibrillator illustrated in FIG. 2. Separating connector block 110 and connector 122 is a pierceable grommet 126, which prevents fluid leakage between connector blocks 122 and 110.

As illustrated in FIG. 3, when a conventional subcutaneous lead 34 is employed in conjunction with the implantable pacemaker/cardioverter/defibrillator, the housing 30 of the device is electrically isolated from the cardioversion/defibrillation output circuitry. The device can thus safely be handled, with a subcutaneous electrode being used for pre-implant screening and testing, without endangering the physician or other medical personnel during delivery of defibrillation shocks.

FIG. 4 illustrates the same connector block assembly as illustrated in FIG. 3, but with lead 34 removed, and a sealing plug 140 inserted. The sealing plug includes a cylindrical section 142 provided with three sealing rings, sealing connector bore 104. The sealing plug is further provided with an elongated conductive pin 144 which bridges connector block 128 and connector 122. As illustrated, the pin 144 pierces the grommet 126. All other labelled structures correspond to identically labelled structures in FIG. 3.

As can be seen, insertion of the sealing plug 140 not only seals connector bore 104 from fluid leakage, it also provides a current path from connector block 122 to connector block 110 and then, via jumper wire 128 to the housing 30 of the implantable pacemaker/cardioverter/defibrillator, so that defibrillation and cardioversion shocks may be delivered between the right ventricular electrode 46 (FIG. 2) and the housing 30 (FIG. 2) of the device.

Figure 6:
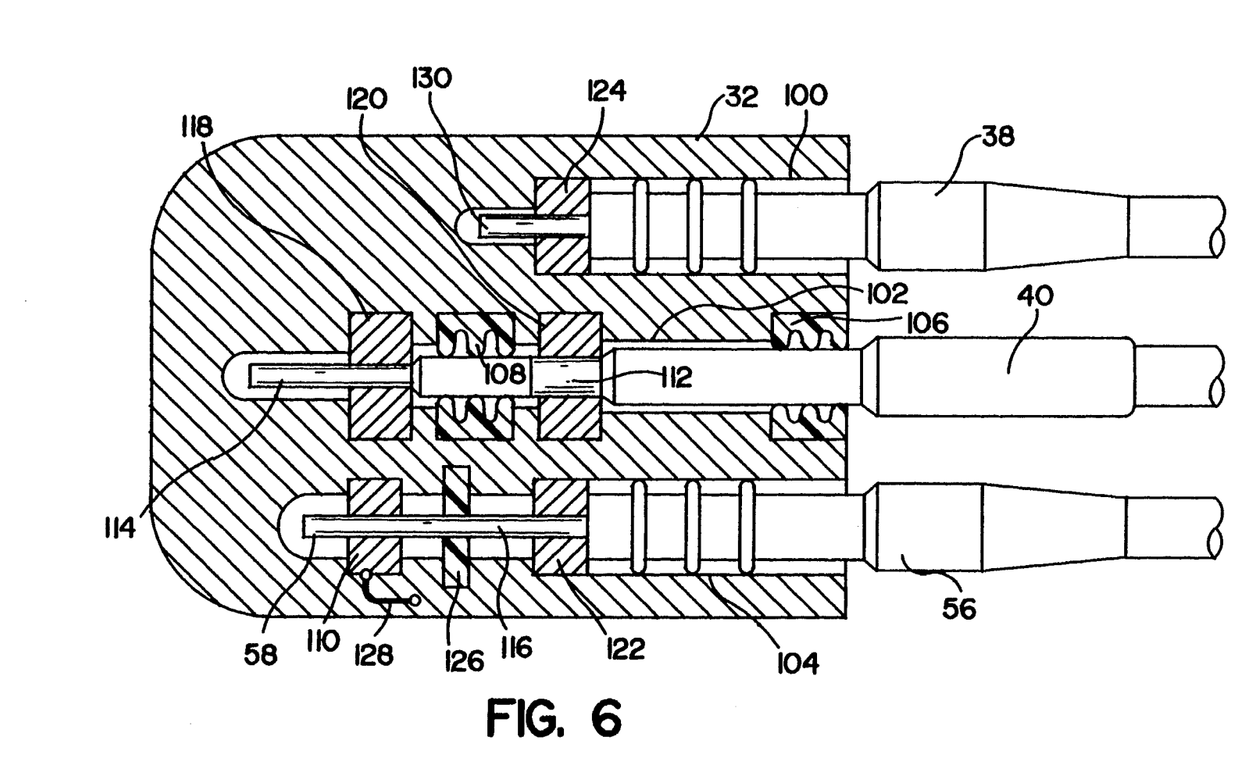
FIG. 6 is a cutaway view of the connector assembly illustrated in FIGS. 3 and 4, with an alternate lead inserted therein.

FIG. 5 illustrates the implantable pacemaker/cardioverter/defibrillator of FIG. 2, with a superior vena cava lead 52 substituted for the subcutaneous lead 34 (FIG. 2). Lead 52 is provided with an elongated coil electrode 54. Lead 52 may employ a connector assembly corresponding to the connector assembly of lead 34, as illustrated in FIG. 3, and simply function to connect the superior vena cava electrode 54 to the cardioversion/defibrillation output circuitry to provide an electrode system for delivering shocks between the right ventricle and superior vena cava. Alternatively, as illustrated in FIG. 6, lead 52 may be provided with an elongated connector pin, providing for connection of the housing 30 of the pacemaker/cardioverter/defibrillator and electrode 54 in common to one terminal of the output of the defibrillation/cardioversion output circuitry. In this case, a three electrode simultaneous pulse system is provided, similar to that illustrated in U.S. Pat. No. 4,953,551, issued to Mehra, et al., without any necessity to internally reprogram or reconfigure the device.

FIG. 6 illustrates the same connector assembly illustrated in FIGS. 3 and 4, but with the proximal end of lead 56 inserted into connector bore 104. The proximal end of lead 56 is provided with an elongated conductive pin 58, which pierces grommet 122 and couples connector block 122 to housing 30. Connector pin 58 is also coupled to superior vena cava electrode 54. Thus, a defibrillation pulse, when delivered, is delivered between electrode 46 (FIG. 5) and electrode 54 and housing 30 (FIG. 5) which are coupled together.

Thus, the embodiment of the invention illustrated in FIGS. 2-6 provides for the ability to reconfigure an implantable cardioverter/defibrillator from a two electrode to a three electrode system, provides the ability to reconfigure the device from a two electrode system to a second two electrode system and further, in this embodiment provides an added safety benefit in that it allows for electrical isolation of the housing 30 of the device, during initial screening and testing prior to implant. The disclosed embodiment provides all of these benefits without the necessity of switching circuitry within the device itself, and thus provides a simple and elegant method of enhancing the performance of pre-existing implantable cardioverters and defibrillators, which may not be provided with such internal switching circuitry.

Figure 7:
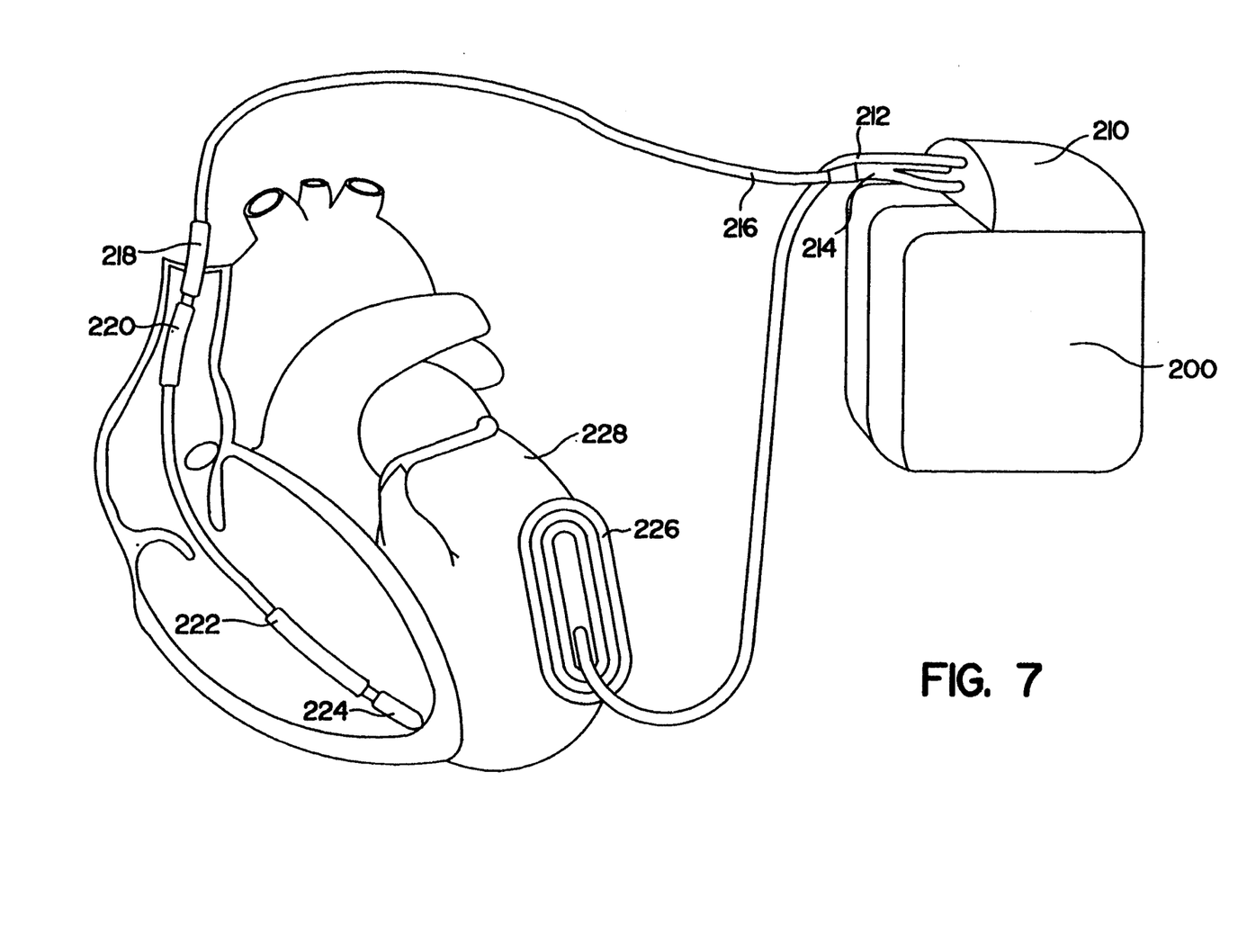
FIG. 7 illustrates an implantable pacemaker/cardioverter/defibrillator and an associated lead system in conjunction with the human heart.

FIG. 7 illustrates an implantable pacemaker/cardioverter/defibrillator employing a second embodiment of the present invention. Like the device illustrated in FIG. 2, it is provided with a conductive housing 200 and a molded connector housing 210 which has three connector bores. As illustrated, the device is provided with a lead system including a defibrillation lead 216 which carries two electrodes located in the superior vena cava 218 and 220, and two electrodes located in the right ventricle 222 and 224. Electrodes 218 and 220 are connected in common to one of three conductors within lead 216. Electrodes 222 and 224 are separately connected to two other insulated conductors within the lead body. In general, the lead may correspond to the lead illustrated in U.S. Pat. No. 4,727,877, issued to Kallok et al, incorporated herein by reference in its entirety. At the proximal end of the lead is a bifurcated connector assembly 214 inserted in two of the connector bores of the connector housing 210. An epicardial electrode lead 212 is also provided, including an epicardial electrode 226, which may correspond to the electrode illustrated in U.S. Pat. No. 4,817,631, issued to Holleman et al., also incorporated herein by reference in its entirety. Alternately, the epicardial electrode lead may take the form of an apex cup electrode, for example an electrode corresponding to that disclosed and claimed in U.S. Pat. No. 4,641,565, issued to Smits, and also incorporated herein by reference in its entirety.

In this second embodiment of the invention, defibrillation pulses may be delivered between electrodes 218 and 220, connected in common, and electrode 222 or between electrodes 218 and 220, connected in common, and electrode 226. Electrodes 222 and 224 may also be employed for cardiac pacing and sensing.

Figure 8:
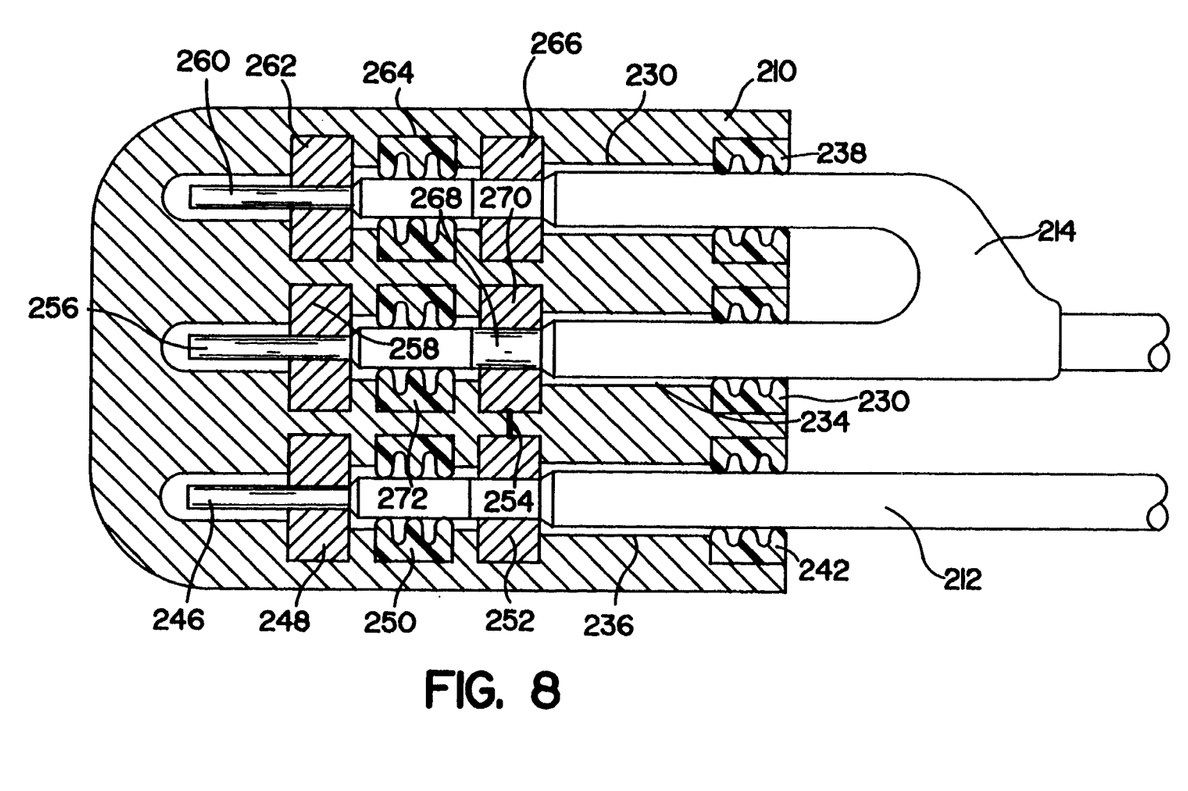
FIG. 8 illustrates a cross-sectional view through the connector housing of the device illustrated in FIG. 7, in conjunction with connectors of the associated lead system.

FIG. 8 illustrates a cross-sectional view through the connector housing 210. As in conjunction with the drawings in FIGS. 3, 4 and 6 above, it is anticipated that the connector bores will not be arranged in a single plane, but will be stacked in a more compact configuration as illustrated in FIG. 7. However, for the sake of easy understanding, they are shown in this fashion in FIGS. 8 and 9.

The connector housing 210 includes three connector bores 230, 234 and 236, each sealed by a set of three sealing rings, 238, 240 and 242, respectively. The bifurcated connector assembly 214 of lead 212 (FIG. 7) is shown inserted into connector bores 230 and 234. Connector bore 230 is provided with two connector blocks 262 and 266. Connector block 262 is coupled to output 22 of cardioversion/defibrillation circuitry 114 in FIG. 1. Connector block 262 is coupled to superior vena cava electrodes 218 and 220, by means of conductive pin 260. Connector block 266, as illustrated, is a spare, which might be employed in the event that a sensor or other lead function requiring an additional conductor were to be included in the lead.

Connector bore 234 is similarly provided with two connector blocks 258 and 266. Connector blocks 258 and 256 are coupled to pacing circuit inputs/outputs 22 and 24 (FIG. 1). Connector block 258 is coupled to electrode 224 (FIG. 7) via connector pin 256. Electrode 224 functions as the active pacing electrode. Connector block 270 is coupled to ventricular electrode 222 (FIG. 7) by means of a connector ring 268. Electrode 222, with the leads inserted as illustrated, functions simply as the indifferent electrode during pacing and sensing. Connector block 270 is also electrically coupled to connector block 252 by means of a jumper wire 254.

Connector bore 236 is provided with two connector blocks 248 and 252. Connector 248 is coupled to cardioversion/defibrillation circuitry output 24 (FIG. 1), and is coupled to patch electrode 226 via connector pin 246. Connector block 252 is not coupled to the output of the cardioversion/defibrillation circuity in this configuration. Sealing rings 264, 272 and 250 serve to prevent fluid leakage between adjacent connector blocks located within individual bores.

With the leads inserted as illustrated, defibrillation pulses are delivered between electrodes 218 and 220 and patch electrode 226, with electrodes 222 and 224 being used only for pacing and sensing. However, in the event that the completely transvenous, endocardial electrode system, lead 212 may be removed and replaced with a sealing plug, as illustrated below in FIG. 9, which in turn connects electrode 222 to the output of the cardioversion/defibrillation circuitry, allowing for cardioversion and defibrillation pulses to be delivered between electrodes 218 and 220, coupled in common, and electrode 222.

Figure 9:
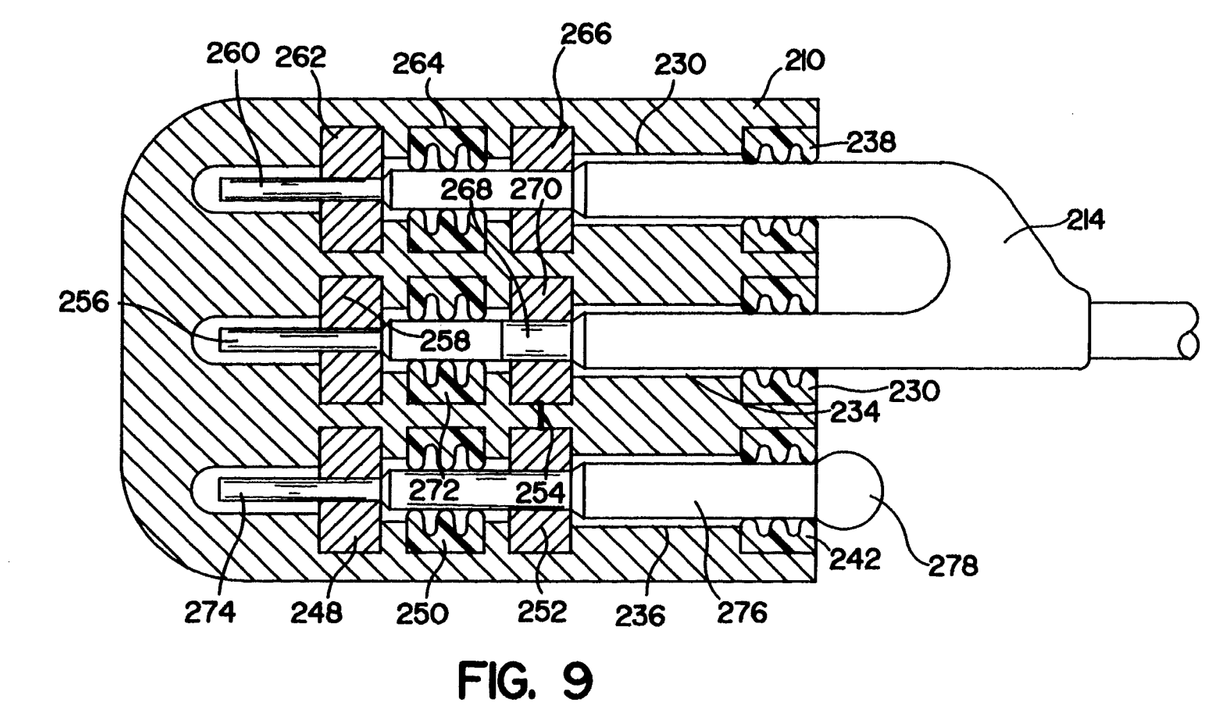
FIG. 9 illustrates the connector assembly of FIG. 8, with a lead removed and a sealing plug inserted.

FIG. 9 illustrates the connector assembly of FIG. 8, with lead 212 removed and sealing plug 278 inserted. All other elements illustrated correspond to identically numbered elements in FIGS. 7 and 8. Like the sealing plug illustrated in FIG. 4, plug 278 is provided with a cylindrical body 276, which in this case engages with sealing rings 242 to provide a fluid seal at the entry of connector bore 236. The plug 278 is also provided with a stepped conductive pin 274 which connects connector block 248 to connector 252 and, by means of jumper wire 254 to connector block 270 and ventricular electrode 222. Thus, with the insertion of plug 278, the unused connector bore is sealed, and the output of cardioversion/defibrillation circuitry 14 (FIG. 1) coupled to connector block 248 is thereby also coupled to electrode 222, providing for an entirely endocardial defibrillation lead system requiring only a single lead. The change in lead configuration is again accomplished without the need for any reprogramming or switching internal to the pacemaker/cardioverter/defibrillator.

Figure 10:
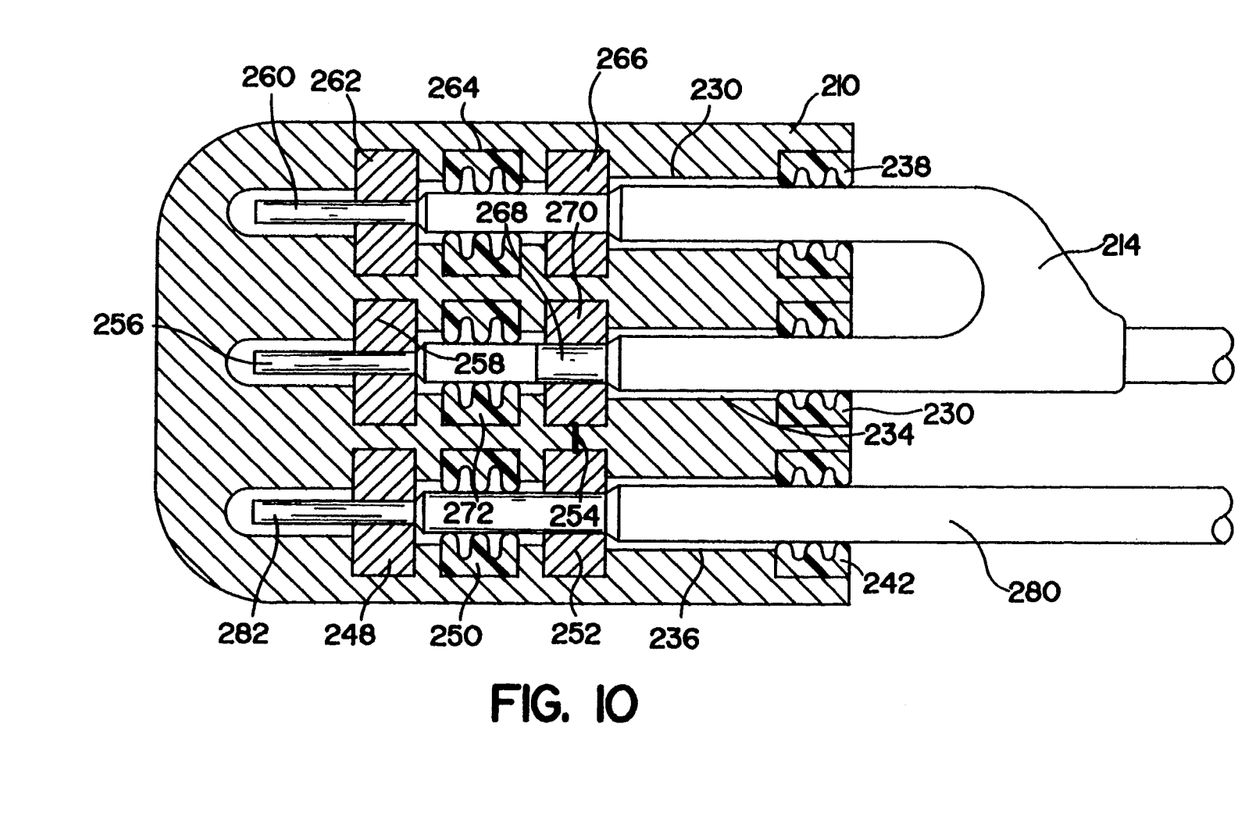
FIG. 10 illustrates the connector assembly of FIG. 8, in conjunction with the connectors of an alternative lead system.

FIG. 10 illustrates the connector assembly of FIG. 8, with lead 212 replaced with a similar epicardial or subcutaneous electrode lead 280. All other elements illustrated correspond to identically numbered elements in FIGS. 7 and 8. Lead 280 corresponds to lead 212 (FIGS. 7, 8) with the exception that the proximal end of the lead is provided with a stepped conductive pin 282 which connects connector block 248 to connector 252 and, by means of jumper wire 254 to connector block 270 and ventricular electrode 222. Connector pin 282 is also coupled to an electrode on lead 280 which may correspond to electrode 226 (FIG. 7). The body of lead 280 engages sealing rings 242 to seal the connector bore 236. Thus, with the insertion of lead 280, the output of cardioversion/defibrillation circuitry 14 (FIG. 1) coupled to connector block 248 is thereby simultaneously coupled to electrodes 222 and 224 on lead 216 (FIG. 7) and to the electrode on lead 280, providing for an multielectrode, simultaneous pulse defibrillation lead system. In this case, pulses are delivered between electrodes 222, 224 and the electrode on lead 280, all coupled in common and electrodes 218 and 220, similarly coupled in common. The change in lead configuration is again accomplished without the need for any reprogramming or switching internal to the pacemaker/cardioverter/defibrillator.

While the above embodiments are all disclosed in the form of connector assemblies which have three connector bores, it is believed that the invention may similarly be practiced in connector assemblies which have more or less than three connector bores. Further, while the disclosed embodiments all employ only a single bore adapted to receive the shorting pin, the invention may be employed multiple times within a single connector assembly. For example, the connector blocks within the assembly may be interconnected in such a fashion that a shorting pin may be inserted in more than one bore, either alternatively or simultaneously to accomplish different switching functions. Similarly, it is believed that the invention may also be practiced in conjunction with connector bores having more than two connectors located within a single connector bore and that shorting pins of different diameters and/or lengths may be employed in such cases to selectively interconnect less than all of the connector blocks associated with an individual connector bore. As such, the above description should be considered exemplary, rather than limiting, with regard to the claims that follow.

In conjunction with above specification, we claim:

1. A medical electrical pulse generator having a conductive housing and having first and second outputs and an associated electrode system including one or more electrode bearing medical electrical leads, comprising:

a connector housing having a plurality of connector bores, including first and second connector bores;

a first electrical connector, coupled to said first output of said pulse generator, and electrically coupled to a first electrode on a said medical electrical lead inserted in said first connector bore;

a second electrical connector, coupled to said second output of said pulse generator;

a conductive member coupled to a second electrode on a said medical electrical lead, inserted within said second connector bore, and coupled to said second electrical connector means;

a third electrical connector coupled to said conductive housing, and coupled to said conductive member inserted in said second connector bore.

2. Apparatus according to claim 1 wherein said conductive means further comprises sealing means for sealing said second connector bore against the ingress of fluids when said conductive means is inserted in said second connector bore.

3. A medical electrical pulse generator having first and second outputs and an associated electrode system including one or more electrode bearing medical electrical leads, comprising:

a connector housing having a plurality of connector bores, including first and second connector bores;

a first electrical connector, electrically coupled to said first output of said pulse generator, and electrically coupled to a first electrode on a said medical electrical lead inserted in said first connector bore;

a second electrical connector, electrically coupled to said second output of said pulse generator;

a conductive member, inserted within said second connector bore, electrically coupled to said second connector means;

third electrical connector, electrically coupled to said conductive member inserted in said second connector bore and electrically coupled to a second electrode on a said medical electrical lead inserted into one of said plurality of connector bores.

4. Apparatus according to claim 3 wherein said conductive member further comprises sealing means for sealing said second connector bore against ingress of fluids when said conductive member is inserted in said second connector bore.

5. Apparatus according to claim 3 wherein said second electrode is located on a said medical electrode lead inserted in a said electrode bore other than said second bore.

6. Apparatus according to claim 3 or claim 5 further comprising a third electrode and wherein said conductive member is electrically coupled to said third electrode.

7. Apparatus for interconnecting a medical electrical pulse generator having first and second outputs with an associated electrode system including one or more medical electrical leads having at least one electrode and a lead connector coupled thereto, comprising:

a connector housing having a plurality of connector bores, including first and second connector bores;

first electrical connector means, coupled to said first output of said pulse generator, for electrically coupling to a lead connector on a medical electrical lead when inserted in said first connector bore;

second electrical connector means, coupled to said second output of said pulse generator, for electrically coupling to a lead connector on a medical electrical lead when inserted in said second connector bore;

third electrical connector means, for coupling to a conductive member when inserted in said second connector bore; and fourth electrical connector means, electrically coupled to said third connector means, for coupling to a lead connector on a medical electrical lead when inserted into one of said plurality of connector bores other than said second connector bore.

8. Apparatus for interconnecting a medical electrical pulse generator having first and second outputs with an associated electrode system including one or more medical electrical leads, comprising:

a connector housing, including a connector bore;

first electrical connector means, coupled to said first output of said pulse generator, for electrically coupling to a conductive member when inserted in said connector bore;

second electrical connector means, not coupled to said pulse generator, for coupling to a conductive member when inserted in said connector bore; and a pierceable grommet located in said connector bore between said first and second connectors.

9. A medical electrical pulse generator having a conductive housing and having first and second outputs and an associated electrode system including a first electrode electrically coupled to said first output, further comprising:

a connector housing having a connector bore;

first electrical connector means, electrically coupled to said second output;

a conductive member inserted within said connector bore and electrically coupled to said first electrical connector means;

a second electrical connector electrically coupled to said conductive housing and coupled to said conductive member; and a second electrode, electrically coupled to said conductive member.

10. Apparatus according to claim 9 wherein said conductive member further comprises means for sealing said connector bore against fluid ingress.

11. Apparatus according to claim 9 further comprising a pierceable grommet located in said bore, between said first and second electrical connectors.

12. A medical electrical pulse generator having first and second outputs and an associated electrode system including a first electrode electrically coupled to said first output; further comprising:

a connector housing having first and second connector bores;

first electrical connector means, electrically coupled to said second output of said pulse generator, for electrically coupling to a lead connector of a medical electrical lead when inserted in said first connector bore;

a conductive member, inserted within said first connector bore, electrically coupled to said first electrical connector means;

second electrical connector means, electrically coupled to said conductive member inserted in said first connector bore; and third electrical connector means, electrically coupled to said second electrical connector means, for electrically coupling to a lead connector on a medical electrical lead when inserted into said second connector bore.

13. Apparatus according to claim 12 wherein said conductive member further comprises means for sealing said first connector bore against fluid ingress.

14. Apparatus according to claim 12 further comprising a medical electrical lead extending from said conductive member and comprising a second electrode, coupled to said conductive member and located on said medical electrical lead.

15. A medical electrical pulse generator having a conductive housing and having first and second outputs and an associated electrode system including a first electrode electrically coupled to said first output, further comprising:

a connector housing having a connector bore;

first electrical connector means, electrically coupled to said second output:

a conductive member inserted within said connector bore and electrically coupled to said first electrical connector means;

a second electrical connector electrically coupled to said conductive housing and coupled to said conductive member; and a pierceable grommet located in said bore, between said first and second electrical connectors.

* * * * *